US011478513B2

(12) United States Patent
Park

(10) Patent No.: US 11,478,513 B2
(45) Date of Patent: Oct. 25, 2022

(54) CUTIBACTERIUM AVIDUM STRAIN, AND COMPOSITION FOR PREVENTING OR TREATING ATOPIC DERMATITIS, COMPRISING STRAIN OR CULTURED PRODUCT THEREOF

(71) Applicant: GENOME AND COMPANY, Gyeonggi-do (KR)

(72) Inventor: Han-Soo Park, Seoul (KR)

(73) Assignee: GENOME AND COMPANY, Gyeonggi-do (KR)

( * ) Notice: Subject to any disclaimer, the term of this patent is extended or adjusted under 35 U.S.C. 154(b) by 5 days.

(21) Appl. No.: 17/270,516

(22) PCT Filed: May 24, 2019

(86) PCT No.: PCT/KR2019/006239
§ 371 (c)(1),
(2) Date: Feb. 23, 2021

(87) PCT Pub. No.: WO2020/040407
PCT Pub. Date: Feb. 27, 2020

(65) Prior Publication Data
US 2021/0299189 A1    Sep. 30, 2021

(30) Foreign Application Priority Data
Aug. 23, 2018    (KR) ..................... 10-2018-0098879

(51) Int. Cl.
*A61K 35/74* (2015.01)
*A61P 17/00* (2006.01)
*C12N 1/20* (2006.01)
*A61K 8/37* (2006.01)
*A61K 8/99* (2017.01)
*A61K 31/216* (2006.01)

(52) U.S. Cl.
CPC .............. *A61K 35/74* (2013.01); *A61K 8/375* (2013.01); *A61K 8/99* (2013.01); *A61K 31/216* (2013.01); *A61P 17/00* (2018.01); *C12N 1/205* (2021.05)

(58) Field of Classification Search
None
See application file for complete search history.

(56) References Cited

U.S. PATENT DOCUMENTS

2003/0175305 A1    9/2003  Garner et al.
2016/0338979 A1    11/2016  Huang

FOREIGN PATENT DOCUMENTS

| JP | 2018-522919 A | 8/2018 |
| KR | 10-1925135 B1 | 12/2018 |
| WO | WO-2017/025936 A2 | 2/2017 |

OTHER PUBLICATIONS

Cosmeticobs "Excipient" 1pg. 2009 accessed atcosmeticobs.com/en/articles/cosmetics-glossary-5/ excipient-321 (Year: 2009).*
Drugs.com "Water" 1 pg. 2021 accessed at drugs.comjinactive/water-112.html (Year: 2021).*
Corvec, S., "Clinical and Biological Features of *Cutibacterium* (Formerly *Propionibacterium*) *avidum*, an Underrecognized Microorganism", Clinical Microbiology Reviews, Jul. 2018, vol. 31, Issue 3, pp. 1-42.
Eady, E. A., et al.; "Inhibitors produced by propionibacteria and their possible roles in the ecology of skin bacteria", Proceedings of the Royal Society of Edinburgh, 79B, 193-199, 1980.
Fujimura, S., et al.; "Purification and Properties of a Bacteriocin-Like Substance (Acnecin) of Oral *Propionibacterium acnes*" Antimicrobial Agents and Chemotherapy, Dec. 1978, pp. 893-898, vol. 14, No. 6.
Ko, H. L., "Propionicins, bacteriocins produced by Propionibacterium avidum", Zentralbl Bakteriol Prig. A., Sep. 1978, 241 (3), 325-8.
Shehadeh, N. H., et al.; "The Bacteriology of Acne", Arch Dermatol. 1963; 88(6):829-831.
Spergel, J. M., et al.; "Atopic dermatitis and the atopic march", J Allergy Clin Immunol, vol. 112, No. 6, pp. S118-S127, 2003.
Bernard, P., et al.; "Antibiotic susceptibility of *Staphylococcus aureus* strains responsible for cutaneous infections in the community", 2008, 135, pp. 13-19.
International Search Report from corresponding PCT Application No. PCT/KR2019/006239, dated Aug. 28, 2019.
Achermann Yvonne et al: "Propionibacterium avidum: A Virulent Pathogen Causing Hip Periprosthetic Joint Infection", Clinical Infectious Diseases, vol. 66, No. 1, Jan. 6, 2018, pp. 54-63.
Ordogh Lilla et al: "Complete Genome Sequence of Propionibacterium avidum Strain 44067, Isolated from a Human Skin Abscess", Genome Announcements, vol. 1, No. 3, Jun. 27, 2013.
Christian F. P. Scholz et al: "The natural history of cutaneous propionibacteria, and reclassification of selected species ~", Internatinoal Journal of Systematic and Evolutionary Microbiology vol. 66, No. 11, Nov. 1, 2016, pp. 4422-4432.

* cited by examiner

*Primary Examiner* — Thane Underdahl
(74) *Attorney, Agent, or Firm* — Harness, Dickey & Pierce, P.L.C.

(57) ABSTRACT

The present invention relates to *Cutibacterium avidum* GENSC01 strain (KCTC 13596BP). The present invention also relates to a composition comprising the strain or its culture, and use thereof. The present invention is effective in improvement, prevention or treatment of atopic dermatitis, acne or skin inflammation by fine dust.

11 Claims, 12 Drawing Sheets

Specification includes a Sequence Listing.

```
gacgaacgct ggcggcgtgc ttaacacatg caagtcgaac ggaaaggccc ctttgggggt      60
actcgagtgg cgaacgggtg agtaacacgt gagtaacctg cccttgactt cgggataact     120
tcaggaaact ggggctaata ccggatagga atccttgctg catggtgggg gttggaaagc     180
ttcggcggtt ttggatggac tcgcggctta tcagcttgtt ggtggggtag tggcttacca     240
aggctttgac gggtagccgg cctgagaggg cgaccggcca cattgggact gagatacggc     300
ccagactcct acgggaggca gcagtgggga atattgcaca atgggcggaa gcctgatgca     360
gcaacgccgc gtgcgggatg acggccttcg ggttgtaaac cgctttcagc aggggcgaag     420
cttttgtgac ggtacctgca gaagaagcac cggctaacta cgtgccagca gccgcggtga     480
tacgtagggt gcgagcgttg tccggattta ttgggcgtaa agagctcgta ggtggttgat     540
tgcgtcggaa gtgaaaactt ggggcttaac cctgagcgtg ctttcgatac gggttgactt     600
gaggaaggta ggggagaatg gaattcctgg tggagcggtg gaatgcgcag atatcaggag     660
gaacaccagt ggcgaaggcg ttctctggac ctttcctga cgctgaggag cgaaagcgtg     720
gggagcgaac aggcttagat accctggtag tccacgctgt aaacggtggg tactaggtgt     780
ggggtccatt ccacggattc cgtgccgtag ctaacgcatt aagtaccccg cctggggagt     840
acggccgcaa ggctaaaact caaaggaatt gacggggccc cgcacaagcg gcggagcatg     900
cggattaatt cgatgcaacg cgaagaacct tacctgggtt tgacatggac tgggagtgct     960
cagagatggg tacgcctcct tgtggggctg gttcacaggt ggtgcatggc tgtcgtcagc    1020
tcgtgtcgtg agatgttggg ttaagtcccg caacgagcgc aaccctcgtt cactgttgcc    1080
agcacgttat ggtggggact cagtggagac cgccggggtc aactcggagg aaggtgggga    1140
tgacgtcaag tcatcatgcc ccttatgtcc agggcttcac gcatgctaca atggccggta    1200
caaagagttg cgagcctgtg agggtgagcg aatctcggaa agccggtctc agttcggatt    1260
ggggtctgca actcgaccct atgaagtcgg agtcgctagt aatcgcagat cagcaacgct    1320
gcggtgaata cgttcccggg gcttgtacac accgcccgtc aagtcatgaa agtcggtaac    1380
acccgaagcc ggtggcctaa cctgtgtggg ggagccgtcg aaggtgggac tggtaattag    1440
gactaagtc                                                            1449
```

FIG. 1

CUTIBACTERIUM AVIDUM STRAIN, AND COMPOSITION FOR PREVENTING OR TREATING ATOPIC DERMATITIS, COMPRISING STRAIN OR CULTURED PRODUCT THEREOF

CROSS-REFERENCE TO RELATED APPLICATIONS

This application is a national phase application of PCT Application No. PCT/KR2019/006239, filed on May 24, 2019, which claims priority to Korean Patent Application No. 10-2018-0098879, filed on Aug. 23, 2018. The entire disclosures of the applications identified in this paragraph are incorporated herein by references.

TECHNICAL FIELD

The present invention relates to a new strain newly isolated, identified and evaluated for its efficacy and its culture. In addition, the present invention relates to a composition comprising such a new strain or its culture. More specifically, the present invention relates to a cosmetic composition having various effects such as skin improvement effect and the like, comprising the novel strain or its culture.

BACKGROUND

The inflammatory response in skin begins as an action to defend skin damage when it is caused by physical stimuli or chemicals, bacteria and the like, and a variety of immunocytes and inflammation-inducing cytokines are involved. IL-6 (interleukin-6), IL-8 (interleukin-8), IL-1β (interleukin-β) and the like are representative inflammation-inducing cytokines.

For example, IL-8 expression is induced in various cells such as peripheral blood monocyte, tissue macrophage, NK cell, fibroblast, vascular endothelial cell, and the like, responding to stimulation by inflammatory cytokines. Inflammatory diseases related to increased (for example, excessive) IL-8 level include inflammatory diseases such as inflammatory keratosis (for example, psoriasis), atopic dermatitis, contact dermatitis, and the like.

Atopic dermatitis (AD) is an inflammatory skin disease accompanying itchiness, and it is chronic and it usually begins in infancy. AD has unceasing itchiness as a major symptom, and has a property of repeating recovery and deterioration without a specific reason. Despite of many recent researches on AD, the cause of AD has not been clearly known until now.

The proliferation of *S. aureus* in atopic dermatitis was first described in a 1970s research. In a number of researches, it has been reported that the proliferation of *S. aureus* was found in 30% to 100% lesions of atopic dermatitis patients.

*S. aureus* has been known to act on an epidermal cell to destroy a skin barrier function or to act as a superantigen on a T cell to induce an inflammation response.

The research that the colonization and inflammation of the *S. aureus* representatively induces deterioration of atopic dermatitis and eczematous dermatitis and causes asthma and food allergy when progressed as long-term chronic inflammation has been reported. In addition, it has been reported that *S. aureus* was detected in a large amount, in microorganism culturing for patients suffering from skin diseases such as folliculitis, furunculosis, impetigo, paronychia, ecthyma and the like. It has been known that *S. aureus* is clinically related to various inflammatory skin diseases, in addition to atopic diseases (1. Atopic dermatitis and the atopic march. J. Allergy Clin. Immunol. 2003, 2. Antibiotic susceptibility of *Staphylococcus aureus* strains responsible for community-acquired skin infections. Ann Dermatol Venereol. 2008).

Thus, it is expected that inhibition of proliferation of *S. aureus* for atopic dermatitis patients in advance may help positively by preventing deterioration of diseases or lowering the severity of diseases.

Lack of filaggrin and modification of filaggrin gene have been well known to be closely related to occurrence and progression of atopic dermatitis in the art. Filaggrin is a moisturizing component comprised in keratinocytes that make up a skin barrier, and is a protein which plays an important role in formation of stratum corneum together with proteins such as keratin, involucrin, loricrin, and the like. Reduction of the amount of expression of filaggrin causes changes in function and moisturization of the skin barrier and leads to various lesions. In particular, formation of a normal skin barrier plays an important role in defense against external stimuli, and when this function is lost, it plays a key role in progression of atopy. Filaggrin is a target of effective improvement of atopic dermatitis in that the absorption of an antigen through skin is an important factor in the increase of atopic dermatitis.

Furthermore, in a recent research, it has been reported that the abnormality of expression of claudin 1 gene (claudin 1, CDN1) as well as the effect by filaggrin protein of atopic dermatitis patients are closely related to atopic dermatitis. By normal expression of the filaggrin and claudin 1 gene, it is possible to intensify the skin barrier function and enhance the water retention of skin and skin moisturizing effect.

On the other hand, *Cutibacterium avidum* has been known as one of skin flora-derived bacteria, and until now, it has been known as a causative bacterium (pathogen) of many infections.

SUMMARY

Technical Problem

Accordingly, in order to solve the above problems, the present invention provides a novel strain of *Cutibacterium avidum*, which has been known only as a pathogen in the past.

The present invention provides a composition for improving skin symptoms using a novel strain of *Cutibacterium avidum*, which has been known only as a pathogen in the past, or its culture.

The present invention provides *Cutibacterium avidum* GENSC01 strain or its culture, and a composition comprising thereof, and provides a novel use of *Cutibacterium avidum* GENSC01 strain or its culture.

The present invention provides a use for improvement, treatment or alleviation of atopic dermatitis, acne or inflammatory skin diseases of *Cutibacterium avidum* GENSC01 strain or its culture. The present invention provides a composition for improving, treating or alleviating atopic dermatitis, acne, or inflammatory skin diseases comprising *Cutibacterium avidum* GENSC01 strain or its culture. Specifically, it provides a composition for improving, treating or alleviating inflammatory skin diseases caused by fine dust.

In addition, the present invention is used as a cosmetic composition by using rosmarinic acid in combination to eliminate peculiar smell of the strain.

The present invention provides a more enhanced antibacterial activity than *Staphylococcus aureus* or *Cutibacterium acnes* by using rosmarinic acid in combination, and provides a removal activity of biofilm produced by *Staphylococcus aureus* or *Cutibacterium acnes*.

The present invention provides *Cutibacterium avidum* GENSC01 strain with excellent cell viability when used in combination with rosmarinic acid.

The present invention provides a cosmetic composition for skin moisturizing comprising *Cutibacterium avidum* GENSC01 strain or its culture.

Technical Solution

One embodiment of the present invention provides *Cutibacterium avidum* GENSC01 strain (accession number KCTC 13596BP).

One embodiment of the present invention provides a culture of the *Cutibacterium avidum* GENSC01 strain (accession number KCTC 13596BP).

Until now, *Cutibacterium avidum* has been known as a pathogen which causes an infectious disease. However, interestingly, it has been confirmed that the GENSC01 strain or its culture of the present invention has an effect of skin condition improvement, thereby completing the present invention.

The strain may have an effect of removal or formation-inhibiting of biofilm produced by microorganisms, and may have an antibacterial activity.

The strain may help improve water retention of skin, and may help improve a skin moisturizing effect.

According to one embodiment of the present invention, the *Cutibacterium avidum* GENSC01 strain of the present invention is a microorganism resident in skin, and it has been confirmed that it is a novel strain belonging to *Cutibacterium avidum* through 16S rDNA sequence analysis and API test. The strain was deposited to Korea Research Institute of Bioscience & Biotechnology Korean Collection for Type Cultures (KCTC) on Jul. 24, 2018 and received Accession number KCTC 13596BP.

According to one embodiment, the *Cutibacterium avidum* GENSC01 strain or its culture of one embodiment of the present invention may show an antibacterial activity against *Staphylococcus aureus* or *Cutibacterium acnes*. In another embodiment, it may have an activity of removal or formation-inhibiting of biofilm which is produced by the *S. aureus*.

The colonization and infection of the *S. aureus* may cause atopic dermatitis, impetigo, deterioration of atopic dermatitis, secondary infection of eczema, and various skin inflammations. The colonization and infection of the *S. aureus* may cause or deteriorate atopic dermatitis, folliculitis, impetigo, cellulitis, folliculitis alopecia, ecthyma, mastitis, and the like, but the *Cutibacterium avidum* GENSC01 strain or its culture of the present invention can inhibit the growth of the *S. aureus*, and inhibit formation of biofilm produced by *S. aureus*.

In one embodiment, the *Cutibacterium avidum* GENSC01 strain or its culture of the present invention can exhibit not only the inhibitory effect of growth of a microorganism, but also the effect of removal or formation-inhibiting of biofilm produced by the microorganism.

In one embodiment, the *Cutibacterium avidum* GENSC01 strain or its culture may have an activity of inhibiting, improving or treating atopic dermatitis, acne or inflammatory skin diseases. Specifically, a composition for improving, treating or alleviating inflammatory skin diseases by fine dust is to be provided.

In one embodiment, the present invention provides an antimicrobial composition comprising the *Cutibacterium avidum* GENSC01 strain or its culture as an active ingredient.

In one embodiment, the present invention provides a composition for treating, preventing or improving atopic dermatitis, acne or inflammatory skin diseases comprising the *Cutibacterium avidum* GENSC01 strain or its culture as an active ingredient. Specifically, a composition for improving, treating or alleviating inflammatory skin diseases by fine dust is to be provided.

The term "culture" of the present invention means a total medium comprising the strain, strain extract, its metabolite, extra nutriments and the like, obtained by culturing the strain during a certain period in a medium capable of supplying nutriments so that the *Cutibacterium avidum* GENSC01 strain can grow and survive, but includes a culture solution in which the strain is eliminated after culturing the strain.

The culture solution may mean only the upper layer liquid collected except for the sunken lower layer by leaving it for a certain time, or one in which microbial cells are removed through filtration, or only the upper part of liquid centrifuged to remove the lower part of precipitation.

The culture solution may be used as a concentrate by concentration by common methods.

The culture solution or concentrate of the culture solution may be provided as a dried material by drying by common methods.

The "culture" mentioned herein may include a culture solution of a microbial cell, a concentrate of culture solution, a dried material of the culture solution or concentrate, unless otherwise mentioned. The culture may comprise a microbial cell in some cases, and may not comprise it, and the inclusion of a microbial cell is not particularly a problem.

The "microbial cell" means the strain of the present invention itself, and it includes the isolated and selected strain itself or a strain isolated from the culture solution by culturing the strain. The microbial cell may be obtained by collecting the lower sunken part by centrifugation, or may be obtained by leaving it for a certain time and removing the upper liquid, as it is sunken in the lower layer of the culture solution by gravity.

According to one embodiment, the culture of the *Cutibacterium avidum* GENSC01 strain of the present invention may use a medium easily selected according to a purpose by those skilled in the art among media used for microorganism culturing, and preferably, it may use a medium used for *Cutibacterium* culturing, and more preferably, it may use RCM (Reinforced *Clostridium* Medium) medium, TSB (Tryptic soy broth) or BHI (Brain Heart Infusion) medium, but not limited thereto.

According to one specific embodiment of the present invention, the culture of the *Cutibacterium avidum* GENSC01 strain of the present invention may be prepared by inoculating the strain of the present invention in the microorganism culturing medium by microorganism culturing methods known in the art (for example, standing culturing, etc.).

The culture of the *Cutibacterium avidum* GENSC01 strain may include a culture solution or a concentrate of the culture solution, and a dried material thereof, and the concentrate or dried material may be easily prepared by concentration or drying methods of a microorganism or culture solution known in the art.

One embodiment of the present invention provides a composition comprising *Cutibacterium avidum* GENSC01 strain or its culture, and preferably, a cosmetic composition, a food composition or a pharmaceutical composition.

The cosmetic composition or pharmaceutical composition may be used as a skin external preparation, and it may be directly applied to an affected area. For example, it may be prepared in various forms such as ointment, cream, emulsion and the like.

In other embodiment, the pharmaceutical composition may be absorbed in the body by oral or parenteral administration, and for example, it may be administered in a non-limiting form such as powders, granules, capsules, injections and the like.

The form of the cosmetic composition or pharmaceutical composition is not particularly limited.

The cosmetic composition may inhibit or improve atopic dermatitis or inflammatory skin diseases.

The cosmetic composition may inhibit or improve atopic dermatitis or inflammatory skin diseases. The examples of the inflammatory skin diseases include inflammatory keratosis (for example, psoriasis), staphylococcal scalded skin syndrome, contact dermatitis, bacterial dermatitis, impetigo, deterioration of atopic dermatitis, secondary infection of eczema, folliculitis alopecia, ecthyma, mastitis, folliculitis, and the like.

The cosmetic composition may have an antibacterial activity against *Staphylococcus aureus* or *Cutibacterium acnes*, or have an activity of removal or formation-inhibiting of biofilm produced by *Staphylococcus aureus* or *Cutibacterium acnes*.

One embodiment of the present invention provides an antimicrobial composition comprising *Cutibacterium avidum* GENSC01 strain (KCTC 13596BP) or its culture.

The antimicrobial composition may have an antimicrobial activity against *Staphylococcus aureus* or *Cutibacterium acnes*.

One embodiment of the present invention may use *Cutibacterium avidum* GENSC01 strain (KCTC 13596BP) or its culture together with rosmarinic acid.

One embodiment of the present invention may reduce the unique odor of the GENSC01 strain or its culture by using rosmarinic acid together.

One embodiment of the present invention may inhibit the growth of *S. aureus* more effectively by using rosmarinic acid together.

Surprisingly, the rosmarinic acid has no toxicity and has an excellent antimicrobial activity, when used together with the GENSC01 strain of the present invention.

One embodiment of the present invention provides a cosmetic composition comprising *Cutibacterium avidum* GENSC01 strain (KCTC 13596BP) or its culture, and rosmarinic acid.

The composition may comprise the *Cutibacterium avidum* GENSC01 strain or its culture, and rosmarinic acid at a weight ratio of 1:0.000001 to 1:0.01 for the purpose of the present invention.

The cosmetic composition may be used in a variety of cosmetics as the unique odor of the strain is eliminated.

One embodiment of the present invention provides a cosmetic composition for skin moisturizing comprising *Cutibacterium avidum* GENSC01 strain (KCTC 13596BP) or its culture. The cosmetic composition may further comprise rosmarinic acid.

Advantageous Effects

The present invention has confirmed that a novel strain of *Cutibacterium avidum* and its culture are effective in improvement, inhibition or treatment of atopic dermatitis symptoms. In addition, it has been confirmed that the novel strain of *Cutibacterium avidum* and its culture are effective in acne improvement. The present invention provides a composition for improving, treating or alleviating inflammatory skin diseases by fine dust, comprising a novel strain of *Cutibacterium avidum* and its culture.

The present invention has confirmed a novel strain of *Cutibacterium avidum*, and it has found an effect of improving skin symptoms using the strain or its culture. Accordingly, the present invention can provide a novel strain of *Cutibacterium avidum*, having a skin improvement function. In addition, the present invention provides a composition for improvement, treatment or alleviation of atopic dermatitis and inflammatory skin diseases comprising a novel strain of *Cutibacterium avidum*, or its culture. Furthermore, the present invention can not only anticipate a synergic effect for its use, but also eliminate the unique odor of the strain, by using it with rosmarinic acid.

BRIEF DESCRIPTION OF THE DRAWINGS

FIG. 1 shows the 16s rRNA sequence of *Cutibacterium avidum* GENSC01 strain (Accession number: KCTC 13596BP) of the present invention.

DETAILED DESCRIPTION

Figure 2:
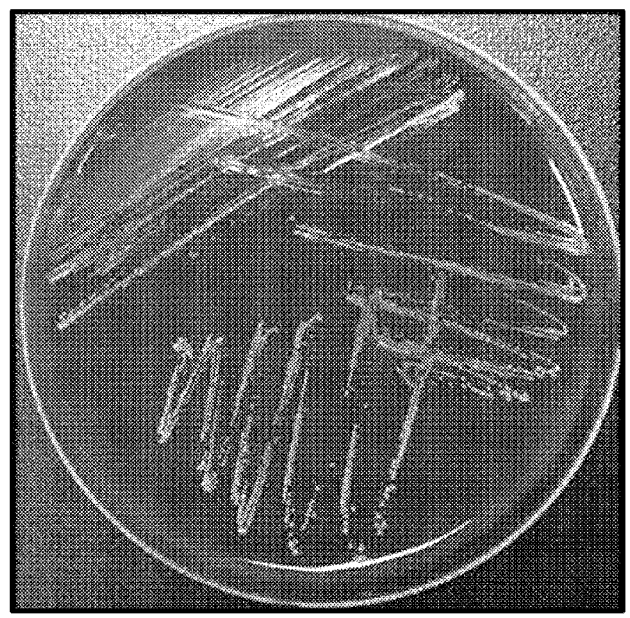
FIG. 2 shows the result of smearing the *Cutibacterium avidum* GENSC01 strain of the present invention on sheep blood agar and culturing it. No transparent ring was found around the microbial cell, and thereby it can be seen that it is not harmful to the human body because there is no hemolysis.

Hereinafter, the present invention will be described by the following examples and the like in order to described it more specifically. However, the examples according to the present invention may be modified to various other forms, and the scope of the present invention should not be construed as being limited to the examples described below. The examples of the present invention are illustratively provided in order to facilitate a specific understanding of the present invention.

[Example 1] Isolation and Identification of *Cutibacteria avidum* GENSC01

1-1. Isolation of Strain

Skin-derived bacteria isolation was carried out from adults who have never had skin diseases such as atopy, psoriasis or acne and the like, or who have not had a history of treatment related to it in the past 6 months. To collect skin samples, unwashed both cheeks and ala nasi were rubbed with a sterile swab dampened with sterilized water by applying a force. The swab was immediately sealed in a test tube containing Reinforced Clostridial Medium (RCM), and the test tube was filled with nitrogen and incubated at 37° C. for 48 to 72 hours. The medium of the test tube containing the cultured swab was streaked on an RCM agar plate by picking it with a platinum loop, and this procedure was repeated 3~4 times to separate pure colonies.

1-2. Identification of Strain

1) Biological Identification Using API Kit

As a method for biochemically identifying an isolated strain, an anaerobic bacterium API 20A kit (biomerieux Co., France) was used. After culturing at 37° C. for 24 hours in a RCM liquid medium of 10 ml and then centrifuging, the medium was removed. After washing with PBS 2~3 times and then $OD_{600}$=3 resuspending with a medium comprised in a kit according to the protocol provided by the manufacturer, it was aliquoted in an appropriate amount to each well of API 20A kit and was anaerobically cultured at 37° C. for 24 hours and then was read.

The final result was identified in a program for identification, API web, and the result was shown in the following Table 1. As the result of identification of API 20A, it was identified as *Propionibacterium* (=*Cutibacterium*) *propionicum/avidum*, and as the result of API ID32, it showed the same biochemical properties as *Propionibacterium avidum*.

TABLE 1

| API 20A reading result | | |
|---|---|---|
| No | Carbohydrates | Utilized |
| 0 | L-tryptophane | − |
| 1 | urea | − |
| 2 | D-glucose | + |
| 3 | D-mannitol | − |
| 4 | D-lactose (bovine origin) | − |
| 5 | D-saccharose (sucrose) | + |
| 6 | D-maltose | + |
| 7 | salicin | − |
| 8 | D-xylose | − |
| 9 | L-arabinose | − |
| 10 | gelatin (bovine origin) | + |
| 11 | esculin ferric citrate | − |
| 12 | glycerol | + |
| 13 | D-cellobiose | − |
| 14 | D-mannose | + |
| 15 | D-melezitose | + |
| 16 | D-raffinose | − |
| 17 | D-sorbitol | − |
| 18 | L-rhamnose | − |
| 19 | D-trehalose | + |

2) A 16s RNA gene sequence was determined by collecting 1 ml of pure culture solution of the identified and isolated strain through a 16s rRNA gene sequence and requesting to Macrogen. Primers for PCR were universal primers of 16s rRNA gene, 27F (5'-AGAGTTTGATCMTGGCTCAG-3') and 1492R (5'-TACGGYTACCTTGTTACGACTT-3'), and 785F (5 '-GGATTAGATACCCTGGTA-3') and 907R (5'-CCGTCAATTCMTTTRAGTTT-3') were used for sequencing. The 16s rRNA sequence of the isolated strain was shown in FIG. 1 and SEQ ID NO: 1, and this strain showed the 99% homology to *Cutibacterium avidum*. Based on the above result, the strain was named "*Cutibacterium avidum* GENSC01" strain, and it was deposited to Korea Research Institute of Bioscience & Biotechnology Korean Collection for Type Cultures (KCTC) on Jul. 24, 2018 and received Accession number KCTC 13596BP.

[Example 2] Hemolysis Test of *Cutibacteria Avidum* GENSC01

A considerable number of *Cutibacterium avidum* strains have hemolytic toxicity and are harmful to the human body depending on strains. To confirm the safety of *Cutibacterium avidum* GENSC01, the presence or absence of hemolytic toxicity was confirmed. The *Cutibacterium avidum* GENSC01 purely cultured in a liquid medium was collected by a platinum loop and it was steaked on a sheep blood agar and it was anaerobically cultured at 37° C. for 48 hours. The hemolysis was determined by the presence of transparent rings around microbial cells, and it was determined that *Cutibacterium avidum* GENSC01 had no hemolysis for sheep blood and therefore it was not harmful to the human body, as could be seen in FIG. 2.

[Example 3] Preparation of Fermented Filtrates of the Strain of the Present Invention

*Cutibacterium avidum* GENSC01 strain was anaerobically cultured on a RCM agar plate at 37° C. for 72 hours. Single colony shown in a solid medium was subcultured in an RCM liquid medium of 10 ml and was cultured under the same condition. 72 hours later, 0.1% was inoculated to the same liquid medium, and it was cultured for 72 hours under the same condition, and the supernatant was centrifuged and filtrated with a 0.22 um pore size filter.

[Example 4] Measurement of Inhibitory Effect of Formation of Biofilm (Selection of Beneficial Bacteria)

A *Staphylococcus aureus* strain (*Staphylococcus aureus* KCTC 1621) was liquid cultured in a titration medium (TSB+0.2% glucose) for 16 to 24 hours. After adding TSB with 0.2% glucose on a 6-well plate (polystyrene), a test group was added to each well in an approximately 5-10% volume. Then, the cultured bacterial solution was inoculated to each well so that the final strain concentration was to be $2 \times 10^6$ CFU/well. Then, it was under static culturing in a 37° C. incubator for 24 hours. After culturing, the culture solution was eliminated and each well was washed twice using sterile PBS of 1~2 ml. After washing, PBS of 2 ml was added and the biofilm was scraped out with a scraper and was suspended, and then the absorbance was measured at 600 nm. The absorbance measurement was conducted using BioPhotometer D30. Untreated wells were used as the negative control group and wells inoculated with baicalein (25 μm/ml) were used as the positive control group to calculate biofilm formation inhibitory ability.

Figure 3:
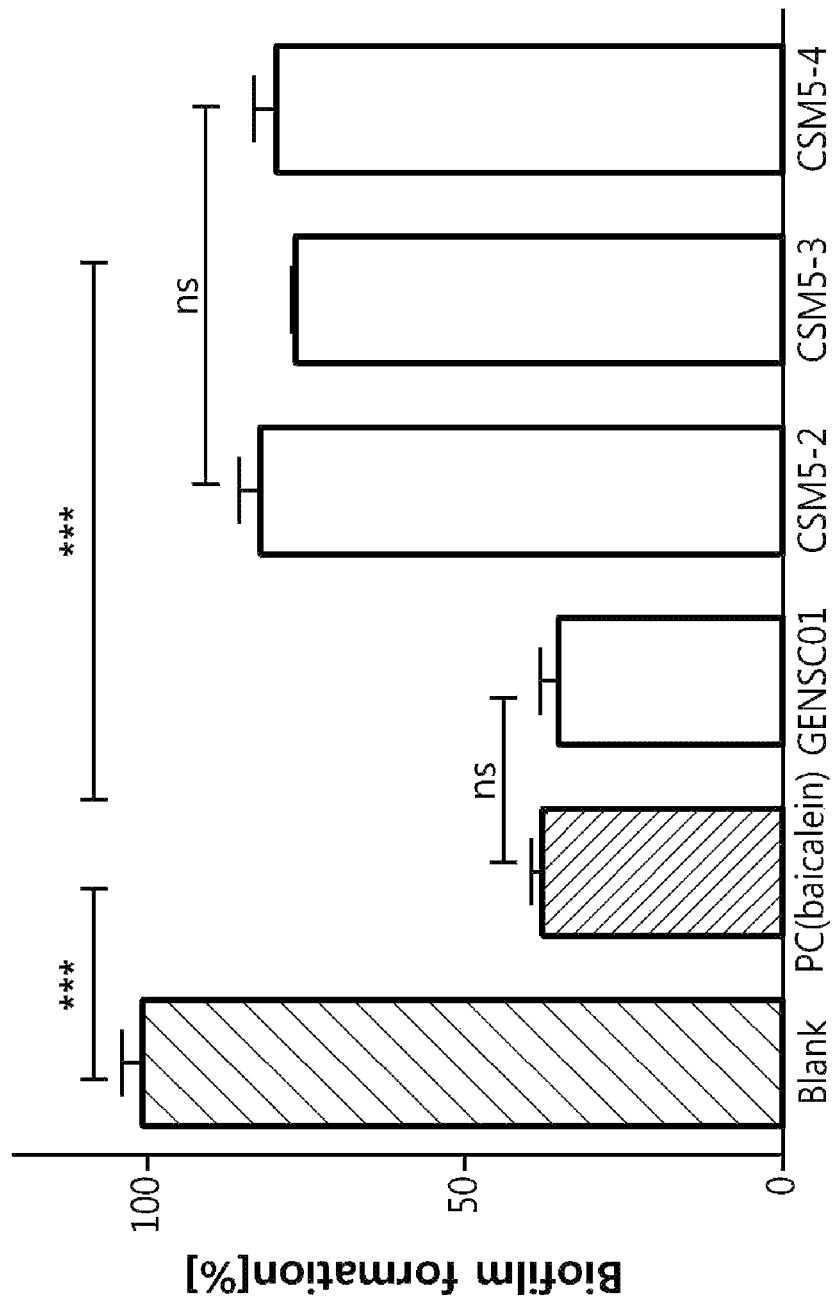
FIG. 3 is the result of comparing the inhibitory effects of formation of biofilm between strains of different each other.

FIG. 3 shows the biofilm formation inhibitory result compared between strains. As can be seen in FIG. 3, it can be found that the GENSC01 strain has the excellent biofilm formation inhibitory ability than other strains.

In other words, compared to the same kind of microorganisms, the GENSC01 of the present invention has the excellent biofilm formation inhibitory effect than other strains. Thus, the strain or its culture of the present invention can exhibit an excellent effect for treatment, improvement or prevention of atopic dermatitis, acne or inflammatory skin disease, than using other strains.

[Example 5] Growth Inhibition on *Staphylococcus aureus* KCTC 1621 and *Cutibacterium acnes* ATCC 6919 (Overlay Clear Zone Test)

Figure 4:
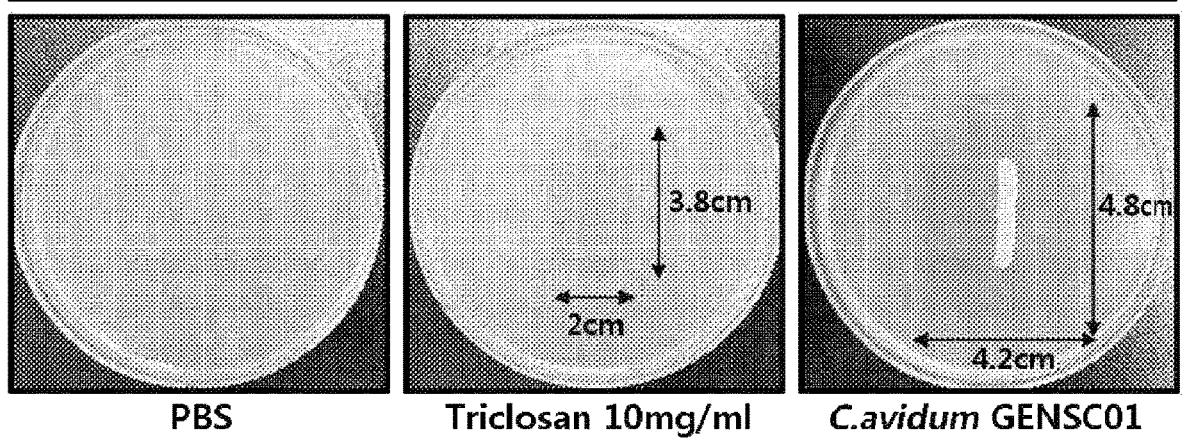
FIG. 4 shows the result of inhibiting the growth for *Staphylococcus aureus* KCTC 1621 by *Cutibacterium avidum* GENSC01 strain.

The effect of growth inhibition of *S. aureus* and *C. acnes* was confirmed by observing formation of a clear zone. When these bacteria are inoculated on an agar medium, bacteria grow in a light color, and therefore the color of the medium becomes cloudy, and it looks transparent if it does not grow. The experiment was progressed, expecting that *S. aureus* and *C. acnes* around *Cutibacterium avidum* GENSC01 could not grow and they became transparent, if *Cutibacterium avidum* GENSC01 had the effect of inhibiting the growth of bacteria. The *Cutibacterium avidum* GENSC01 culture broth was collected with a platinum loop and was anaerobically cultured in a thin RCM agar plate at 37° C. for 72 hours by drawing a line about 2.5 cm. After confirming that *Cutibacterium avidum* GENSC01 sufficiently grew, *S. aureus* and *C. acnes* strains adjusted to $10^4$ cfu/ml were inoculated in 10 ml RCM agar at about 45° C. which was not yet solidified, and they were well suspended before the medium was hardened, and they were evenly solidified by pouring them on the agar plate in which *Cutibacterium avidum* GENSC01 grew. In the solidified agar plate, *S. aureus* and *C. acnes* were further cultured anaerobically at 37° C. for about 40 hours and about 72 hours, respectively, to observe the size of the clear zone appearing around *Cutibacterium avidum* GENSC01. As the negative control group, phosphate-buffered saline (PBS) was used, and as the positive control group, triclosan was used, and *S. aureus* and *C. acnes* were treated at an amount of 10 mg/ml and 200 mg/ml, respectively. As a result, as FIG. 4, the transparent area around the *Cutibacterium avidum* GENSC01 was observed, and the transparency was reduced with distance from *Cutibacterium avidum* GENSC01, thereby confirming that the *Cutibacterium avidum* GENSC01 had an ability of inhibiting growth of *S. aureus*. It could be seen that when treating the negative control group, PBS, the clear zone was not observed, and when treating a bactericide, triclosan as the positive control group, the clear zone was observed, but it had much smaller area than GENSC01 treatment. The result was shown in FIG. 4.

Figure 5:
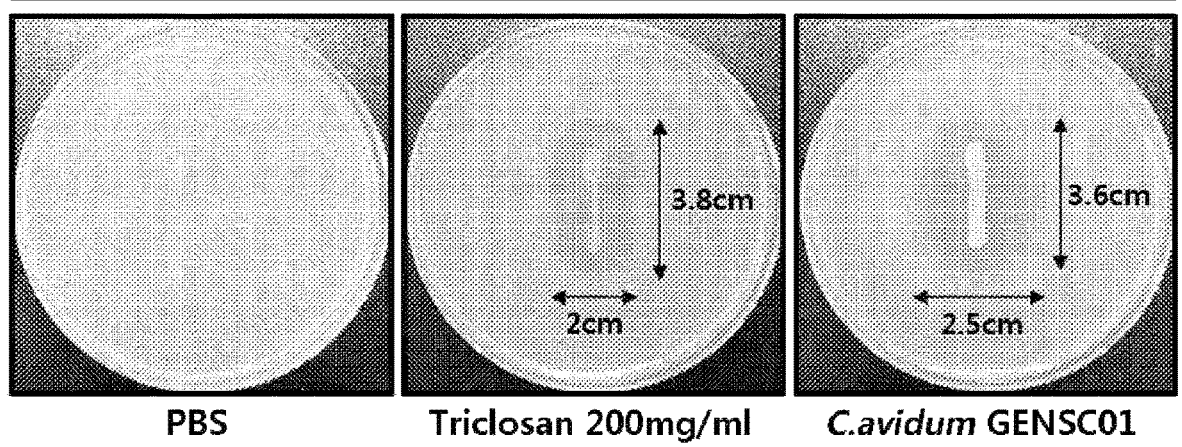
FIG. 5 shows the result of inhibiting the growth for *Cutibacterium acnes* ATCC 6919 by *Cutibacterium avidum* GENSC01 strain.

In addition, as could be seen in FIG. 5, in the result of inoculating *C. acnes*, the transparent area around the *Cutibacterium avidum* GENSC01 was observed, and the transparency was reduced with distance from *Cutibacterium avidum* GENSC01, thereby confirming that the *Cutibacterium avidum* GENSC01 had an ability of inhibiting growth of *C. acnes*. Also, it could be seen that when treating the negative control group, PBS, the clear zone was not observed, and when treating a bactericide, triclosan as the positive control group, the clear zone was observed, but it had much smaller area than GENSC01 treatment.

Through these results, it was confirmed that the *Cutibacterium avidum* GENSC01 of the present invention could provide an effect of improving, preventing or treating acne by inhibiting an acne-causing bacterium, *C. acnes*.

[Example 6] Cytotoxicity Confirmation

To evaluate the cytotoxicity of fermented filtrates prepared in the Example 3, the following experiment was progressed. HaCaT cells were attached on a 96-well cell culture plate for 24 hours at $5 \times 10^3$ cells/well each and then the test group samples were added by concentration to culture it under the condition of 5% $CO_2$ and 37° C. for 48 hours. 48 hours later, the cultured cell medium was removed, and 0.5 mg/ml dimethylthiazol-2-y1)-2-5-diphenyltetrazolium bromide (MTT) formazan solution was treated to cells, and they were reacted for 4 hours, and after the time passage, all the cell medium was removed and the formazan solution was dissolved by DMSO and then the absorbance was measured at 570 nm with SpectraMax M2. Then, the survival rate of the HaCaT cell line was calculated by converting with the equation of $O.D_{sample}/O.D_{control} \times 100$.

Figure 6:
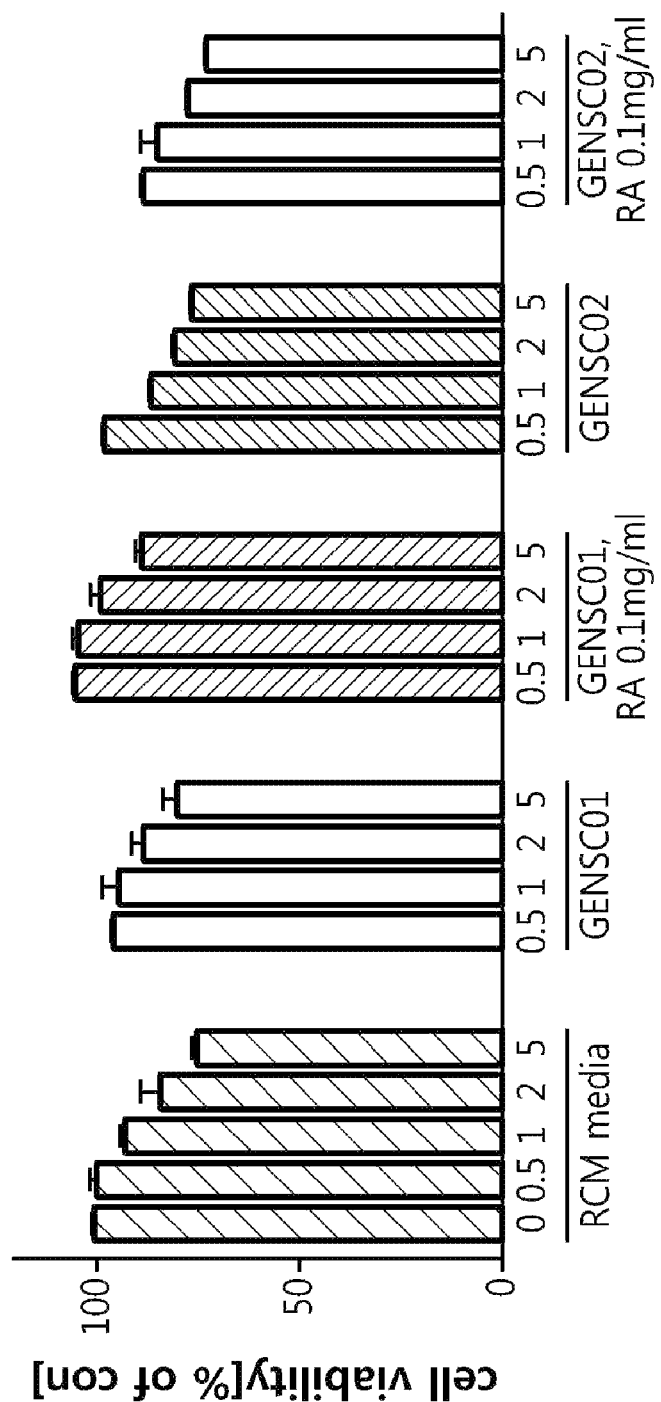
FIG. 6 shows the result of cytotoxicity test of fermented filtrates of *Cutibacterium avidum* GENSC01 strain.

As could be seen in FIG. 6, the treatment of GENSC01 did not affect the survival rate of the HaCaT cell line significantly. Thus, it could be confirmed that GENSC01 had no cytotoxicity.

On the other hand, in case of the experimental group in which rosmarinic acid was added, interestingly, it was confirmed that the cell survival rate could be increased. In other words, it was confirmed that the effect of cytotoxicity reduction could be expected by the addition of rosmarinic acid.

[Example 7] Confirmation of Skin Barrier Function Enhancement Efficacy

In order to investigate the GENSC01 fermented filtrates had a function of skin barrier enhancement for the HaCaT cell line, in addition to the efficacy of inhibiting biofilm of *S. aureus*, the fermented filtrates of GENSC01 were treated to the HaCaT cell line by % to the cell culture solution, and then were reacted for 24 hours to confirm the expression of filaggrin and claudin-1 which were markers of the skin barrier function on RNA.

7-1. Confirmation of Expression Facilitating Efficacy of Filaggrin

Figure 7:
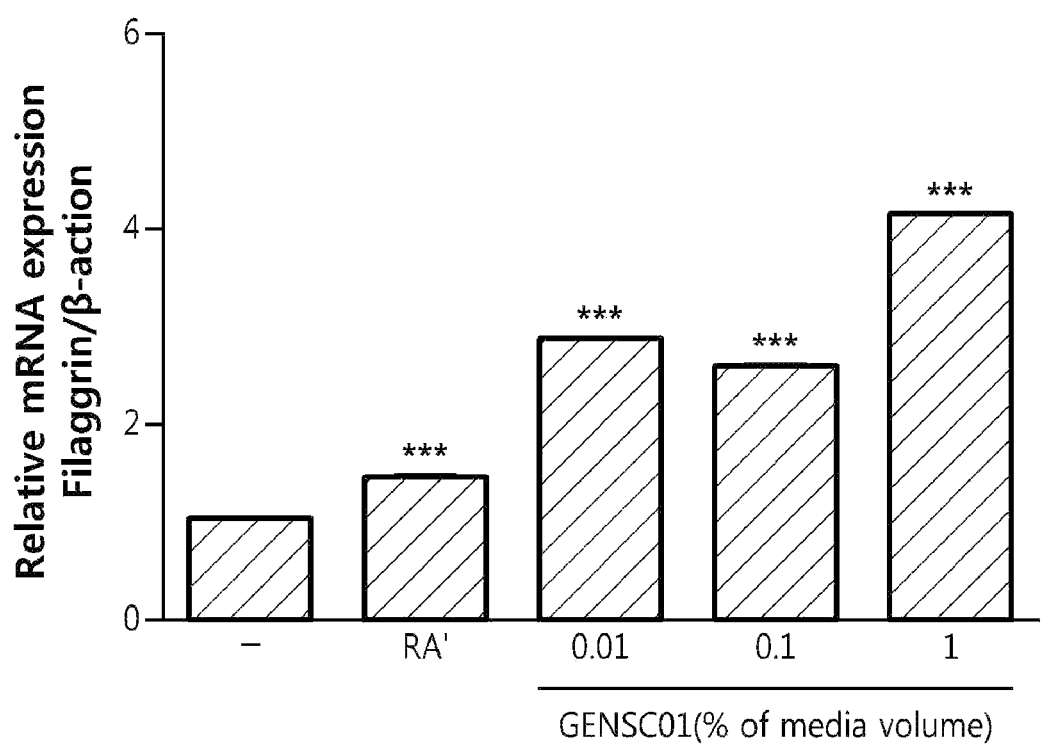
FIG. 7 shows the efficacy of facilitating filaggrin expression of fermented filtrates of *Cutibacterium avidum* GENSC01 strain.

As shown in FIG. 7, it was confirmed that the degree of expression of filaggrin of fermented filtrates increased compared to the positive control group, retinoic acid (RA', 1 μM). FIG. 7 shows the filaggrin expression facilitating efficacy of fermented filtrates. GENSC01 0.01%, 0.1% and 1% were treated, respectively.

As can be seen in FIG. 7, it can be seen that GENSC01 has an excellent filaggrin expression effect compared than retinoic acid (positive control group) known to have an excellent filaggrin expression effect. Through this, GENSC01 can provide an atopic dermatitis improvement effect, an acne improvement effect, a skin barrier enhancement effect, and a skin moisture content maintenance or increase effect by increasing filaggrin expression.

7-2. Confirmation of Expression Facilitating Efficacy of Claudin-1

Figure 8:
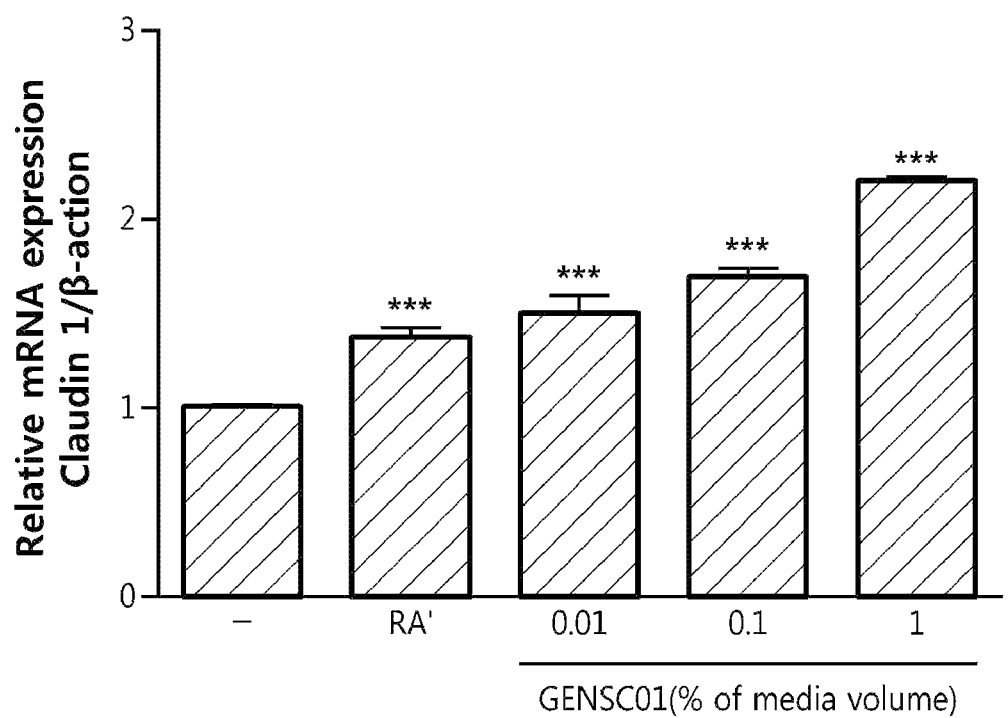
FIG. 8 shows the efficacy of facilitating claudin 1 expression of fermented filtrates of *Cutibacterium avidum* GENSC01 strain.

As shown in FIG. 8, it was confirmed that the claudin expression degree of the fermented filtrates increased in proportion to the concentration, compared to the positive control group, retinoic acid (RA', 1 μM). FIG. 8 shows the claudin expression facilitating efficacy of fermented filtrates.

As can be seen in FIG. 8, it can be seen that GENSC01 has an excellent claudin expression effect compared than retinoic acid (positive control group) known to have an excellent claudin expression effect. Through this, GENSC01 can provide an atopic dermatitis improvement effect, an acne improvement effect, a skin barrier enhancement effect, and a skin moisture content maintenance or increase effect by increasing claudin expression.

[Example 8] Confirmation of Itchiness Alleviation Efficacy

Figure 9:
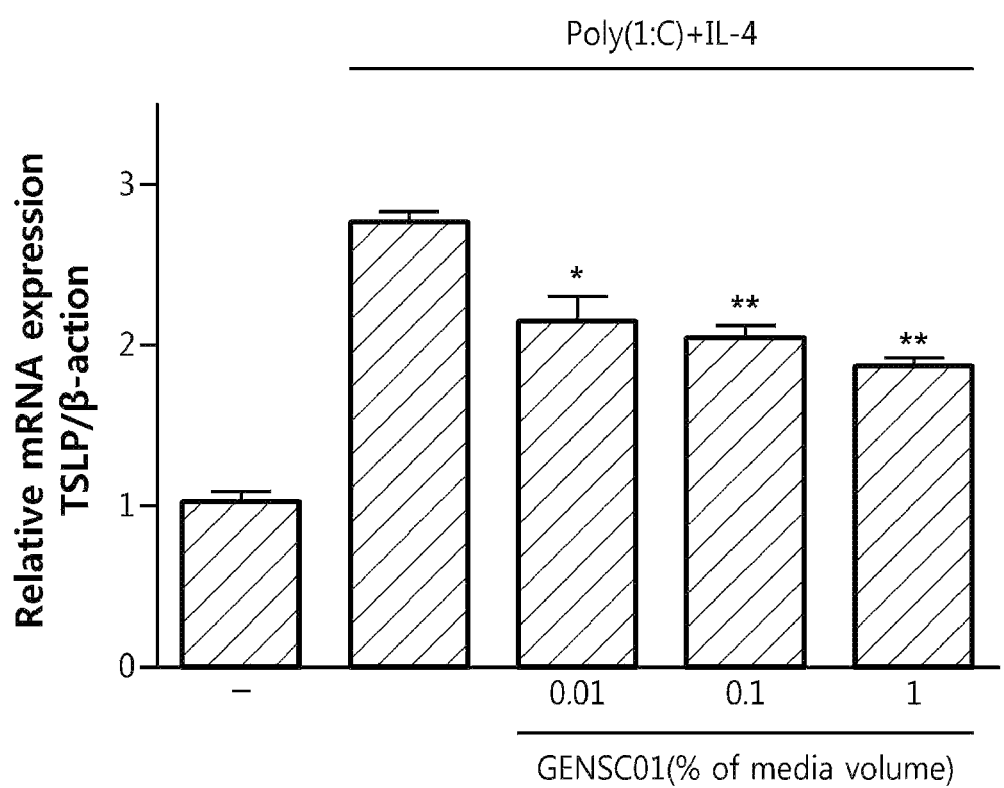
FIG. 9 shows the reduction of TSLP expression of fermented filtrates of *Cutibacterium avidum* GENSC01 strain.

The expression of TSLP, the cytokine acting as one of causes of atopic dermatitis was confirmed on RNA, by treating fermented filtrates of GENSC01 to the HaCaT cell line by % and then reacting for 4 hours. As shown in FIG. 9, it was confirmed that the TSLP expression degree of fermented filtrates was reduced. Thus, it was confirmed that the GENSC01 culture of the present invention inhibited the TSLP expression and solved skin itchiness, thereby having an effect in improvement of atopic dermatitis.

[Example 9] Deodorization Effect of Rosmarinic Acid 9-1. Preparation of Preparations At first, using the fermented filtrates and rosmarinic acid, preparations shown in Table 2 (Comparison 1, Samples 1~3) were prepared and the deodorization function was investigated. The sensory test was carried out by 57 panels, and the test result was shown as an average value after conducting on the basis of fermented filtrates (5%).

TABLE 2

|  | Comparison 1 | Sample 1 | Sample 2 | Sample 3 |
| --- | --- | --- | --- | --- |
| GENSC01 fermented filtrates | 5 parts by weight | | | |
| Rosmarinic acid (Sigma-aldrich, USA) | 0 | 0.0001 part by weight | 0.001 part by weight | 0.01 part by weight |
| Water | | to 100 parts by weight | | |

9-2. Evaluation result

[Evaluation Criteria]

1: No odor.
2: A little odor remains.
3: Odor remains.
4: Most odor remains.
5: No change.

TABLE 3

|  | Sensory test result |
| --- | --- |
| Comparison 1 | 5 |
| Sample 1 | 3.1 |
| Sample 2 | 2.8 |
| Sample 3 | 2.8 |

As shown in the Table 3, the case of treating rosmarinic acid together was effective for unpleasant odor removal, compared to single treatment of GENSC01 fermented filtrates.

[Example 10] Measurement of Biofilm Formation-Inhibiting Effect (Containing Rosmarinic Acid)

The experiment method was same as the method of Example 4, the positive combination effect of the biofilm formation-inhibiting ability of rosmarinic acid and the biofilm formation-inhibiting ability of the fermented filtrates was to be measured.

When treating the rosmarinic acid aqueous solution and fermented filtrates respectively, the effect of inhibiting biofilm formation of the *Staphylococcus aureus* strain of about 35% was shown, compared to the untreated group. As the baicalein treatment group as the positive control showed about 30% inhibitory ability, the result that the effect of rosmarinic acid and fermented filtrates had the similar or better inhibitory ability than the positive control was shown. In addition, in the experimental groups in which the fermented filtrates and rosmarinic acid aqueous solution were mixed (containing rosmarinic acid of A=0.01, B=0.1, C=0.5 mg/ml), compared to the blank group, 50%, 57% and 62% of biofilm formation-inhibiting effect was shown, respectively.

Figure 10:
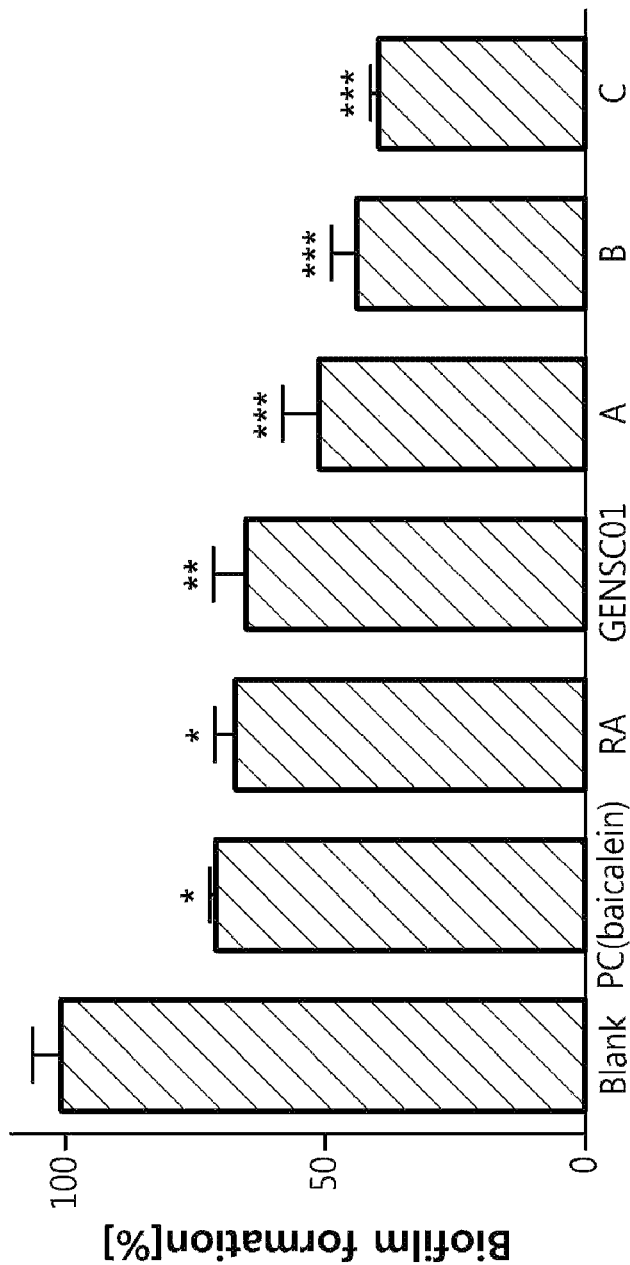
FIG. 10 shows the result which shows that the inhibitory effect of formation of biofilm was excellent when treating fermented filtrates of *Cutibacterium avidum* GENSC01 strain and rosmarinic acid together, than the case of treating each of them alone.

As shown in FIG. 10, it was confirmed that it inhibited the biofilm formation ability of *Staphylococcus aureus* strain more effectively than the cases of treating the rosmarinic acid aqueous solution and fermented filtrates separately.

[Example 11] Anti-Inflammatory Efficacy Evaluation

At first, GENSCO1 fermented filtrates were pre-treated for 1 hour to cells in which $2 \times 10^5$ of HaCaT human keratinocyte lines were attached in a 6-well plate, respectively, by culturing them in a 37° C. and 5% $CO_2$ incubator for 24 hours. Then, the heat-treated *C. acnes* (100MOI) was treated and was reacted for 4 hours. Then, after extracting RNA for each sample, the RNA expression for the inflammation response cytokine factors, IL-6 and IL-8 was confirmed by real-time PCR.

1. IL-8 Expression Rate Confirmation

Figure 11:
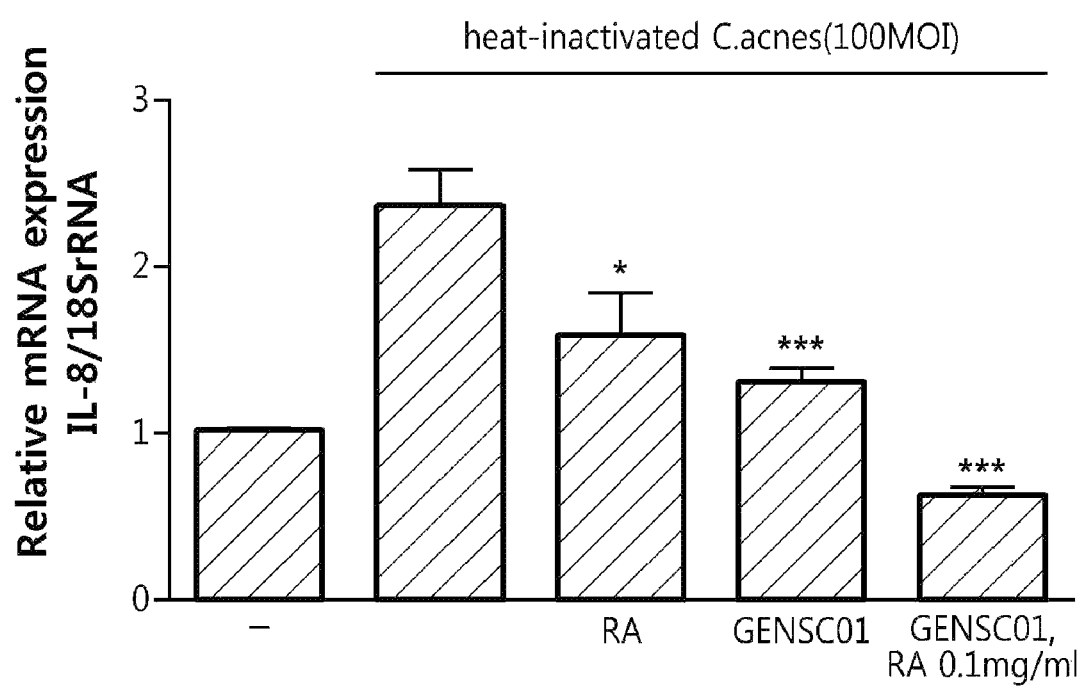
FIG. 11 is the result of confirming the IL-8 expression rate when treating fermented filtrates of *Cutibacterium avidum* GENSC01 strain and rosmarinic acid respectively or together.

As a result, as shown in FIG. 11, it was demonstrated that the inflammation response was reduced in the group treated by the culture filtrates and rosmarinic acid aqueous solution respectively, compared to the control group induced to *C. acnes*. In addition, it was shown that the inflammation response did not occur in the mixed composition of the culture filtrates and rosmarinic acid aqueous solution, compared to single treatment.

2. IL-6 Expression Rate Confirmation

Figure 12:
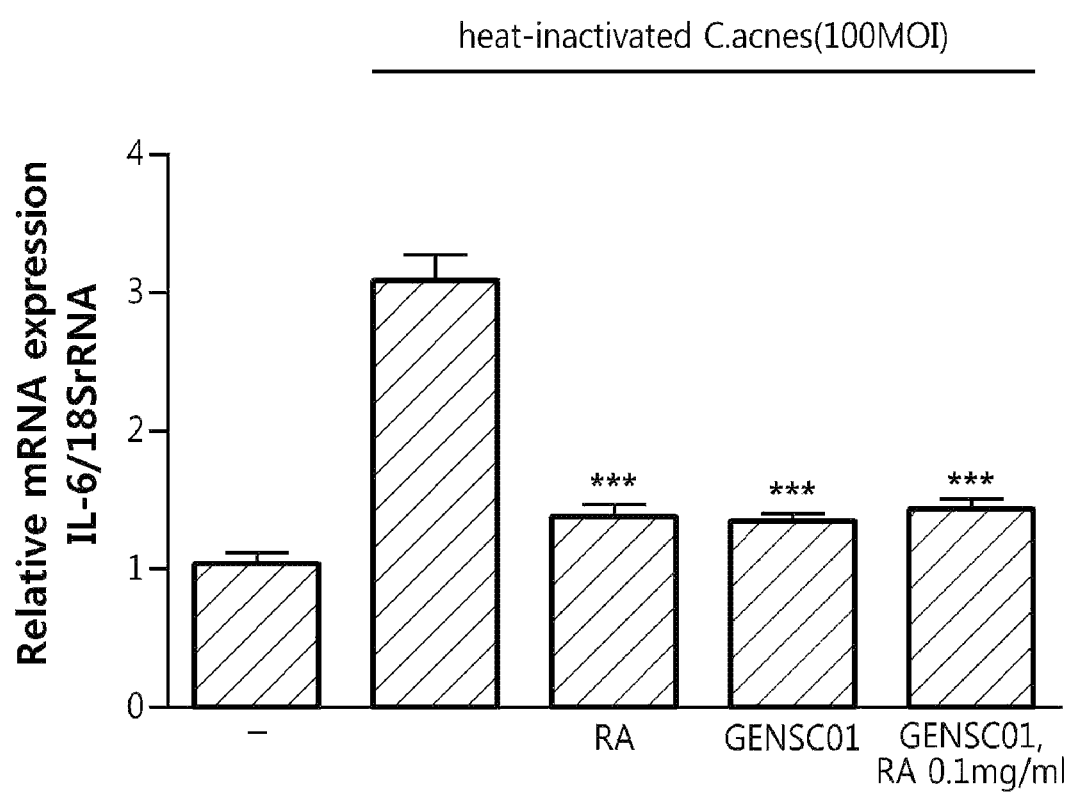
FIG. 12 is the result of confirming the IL-6 expression rate when treating fermented filtrates of *Cutibacterium avidum* GENSC01 strain and rosmarinic acid respectively or together.

The result was shown in FIG. 12. It was confirmed that the expression of IL-6 was reduced at a similar level in the GENSC01 culture filtrates, rosmarinic acid aqueous solution and the mixed composition of the culture filtrates and rosmarinic acid aqueous solution.

[Example 12] Evaluation of Anti-Inflammation Efficacy Against Fine Dust

Figure 13:
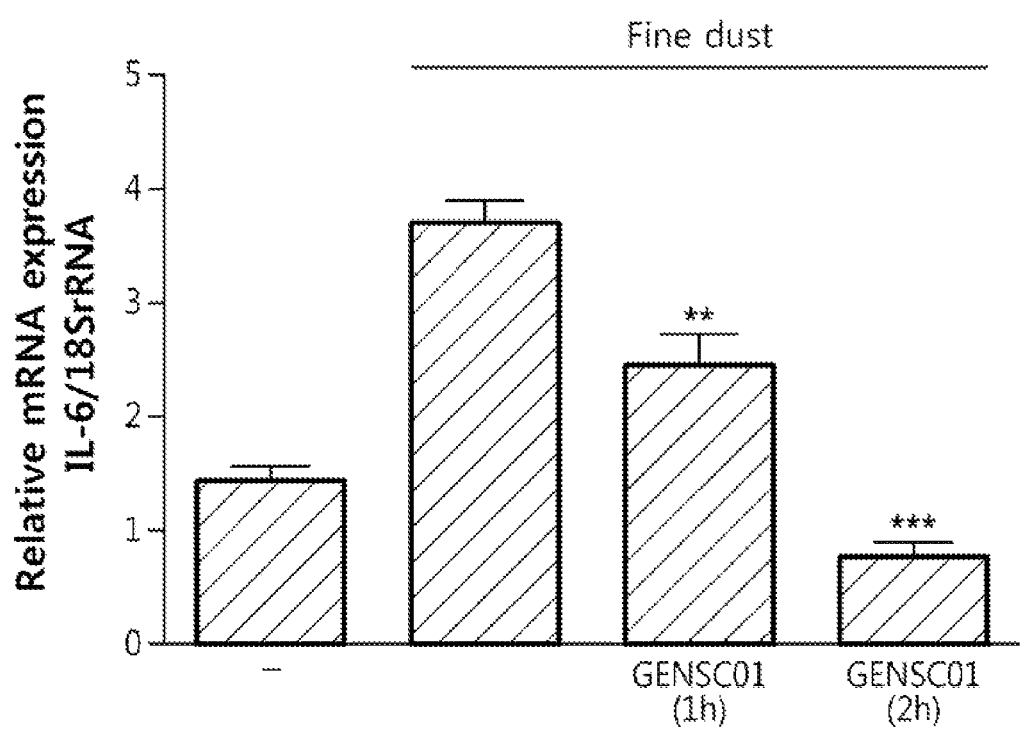
FIG. 13 is the result of confirming that fermented filtrates of *Cutibacterium avidum* GENSC01 strain are effective in reducing inflammation by fine dust.

At first, inflammation was induced by treating fine dust (Aldrich) 50 ug/ml to cells for 2 hours in which $6.5 \times 10^5$ of HaCaT human keratinocyte lines were attached in a 6-well plate, respectively, by culturing them in a 37° C. and 5% $CO_2$ incubator for 24 hours, and then it was washed out 3 times. Then, after treating the GENSCO1 fermented filtrates for 1 hour and 2 hours and then extracting RNA for each sample, the RNA expression for the inflammation response cytokine factor, IL-6, was confirmed by real-time PCR. The result was shown in FIG. 13. It was confirmed that the expression of IL-6 was significantly reduced by the GEN-SCO1 culture filtrates and it was further reduced in case of treatment for 2 hours.

INDUSTRIAL APPLICABILITY

The present invention provides a new *Cutibacterium avidum* strain or its culture which can be used as a cosmetic composition.

The strain or culture of the present invention can be used as a cosmetic composition.

[Accession Number]
Depository institution: Korea Research Institute of Bioscience & Biotechnology
Accession number: KCTC13596BP
Deposit date: 20180724

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method of inhibiting, improving or treating atopic dermatitis or inflammatory skin diseases, comprising:
   administering a subject in need thereof a therapeutically effective amount of *Cutibacterium avidum* GENSCO1 strain (KCTC 13596BP) or its culture.

2. The method according to claim 1, wherein the *Cutibacterium avidum* GENSCO1 strain or its culture has an antibacterial activity against *Staphylococcus aureus* or *Cutibacterium acnes*, or has an activity of removal or formation-inhibiting of biofilm produced by *Staphylococcus aureus* or *Cutibacterium acnes*.

3. The method according to claim 1, wherein the inflammatory skin diseases include skin inflammation by fine dust.

4. The method according to claim 1, wherein *Cutibacterium avidum* GENSCO1 strain (KCTC 13596BP) or its culture is administered with rosmarinic acid.

5. The method according to claim 1, wherein the *Cutibacterium avidum* GENSCO1 strain or its culture, and rosmarinic acid are administered at a weight ratio of 1:0.000001 to 1:0.01.

6. A method of inhibiting the growth of *Staphylococcus aureus* or *Cutibacterium acnes* of skin of a subject, comprising:
   administering to the subject in need thereof a therapeutically effective amount of *Cutibacterium avidum* GENSCO1 strain (KCTC 13596BP) or its culture.

7. The method according to claim 6, wherein *Cutibacterium avidum* GENSCO1 strain (KCTC 13596BP) or its culture is administered with rosmarinic acid.

8. A composition comprising *Cutibacterium avidum* GENSCO1 strain (KCTC 13596BP) or its culture, at least one excipient, and rosmarinic acid.

9. The composition according to claim 8, wherein the composition comprises the *Cutibacterium avidum* GENSCO1 strain or its culture, and rosmarinic acid at a weight ratio of 1:0.000001 to 1:0.01.

10. The composition according to claim 8, which is a pharmaceutical composition.

11. The composition according to claim 8, which is a cosmetic composition.

* * * * *

SEQUENCE LISTING

```
<160> NUMBER OF SEQ ID NOS: 1

<210> SEQ ID NO 1
<211> LENGTH: 1449
<212> TYPE: DNA
<213> ORGANISM: Unknown
<220> FEATURE:
<223> OTHER INFORMATION: 16s rRNA of Cutibacterium avidum GENSC01

<400> SEQUENCE: 1
gacgaacgct ggcggcgtgc ttaacacatg caagtcgaac ggaaaggccc ctttgggggt      60
actcgagtgg cgaacgggtg agtaacacgt gagtaacctg cccttgactt cgggataact     120
tcaggaaact ggggctaata ccggatagga atccttgctc atggtgggg gttggaaagc      180 ttcggcggtt ttggatggac tcgcggctta tcagcttgtt ggtggggtag tggcttacca    240
aggctttgac gggtagccgg cctgagaggg cgaccggcca cattgggact gagatacggc    300
ccagactcct acgggaggca gcagtgggga atattgcaca atgggcggaa gcctgatgca    360
gcaacgccgc gtgcgggatg acggccttcg ggttgtaaac cgctttcagc aggggcgaag    420
cttttgtgac ggtacctgca gaagaagcac cggctaacta cgtgccagca gccgcggtga    480
tacgtagggt gcgagcgttg tccggattta ttgggcgtaa agagctcgta ggtggttgat    540
tgcgtcggaa gtgaaaactt ggggcttaac cctgagcgtg ctttcgatac gggttgactt     600
gaggaaggta ggggagaatg gaattcctgg tggagcggtg gaatgcgcag atatcaggag    660
gaacaccagt ggcgaaggcg gttctctgga cctttcctga cgctgaggag cgaaagcgtg    720
gggagcgaac aggcttagat accctggtag tccacgctgt aaacggtggg tactaggtgt    780
ggggtccatt ccacggattc cgtgccgtag ctaacgcatt aagtaccccg cctggggagt    840
acggccgcaa ggctaaaact caaaggaatt gacgggggcc cgcacaagcg gcggagcatg    900
cggattaatt cgatgcaacg cgaagaacct tacctgggtt tgacatggac tgggagtgct   960
cagagatggg tacgcctcct tgtggggctg gttcacaggt ggtgcatggc tgtcgtcagc    1020
tcgtgtcgtg agatgttggg ttaagtcccg caacgagcgc aaccctcgtt cactgttgcc    1080
agcacgttat ggtggggact cagtggagac cgccgggtc aactcggagg aaggtgggga    1140
tgacgtcaag tcatcatgcc ccttatgtcc agggcttcac gcatgctaca atggccggta    1200
caaagagttg cgagcctgtg agggtgagcg aatctcggaa agccggtctc agttcggatt     1260
ggggtctgca actcgaccct atgaagtcgg agtcgctagt aatcgcagat cagcaacgct    1320
gcggtgaata cgttcccggg gcttgtacac accgcccgtc aagtcatgaa agtcggtaac    1380
acccgaagcc ggtggcctaa cctgtgtggg ggagccgtcg aaggtgggac tggtaattag    1440
gactaagtc                                                            1449
```